US012241765B2

(12) United States Patent
Lee

(10) Patent No.: US 12,241,765 B2
(45) Date of Patent: Mar. 4, 2025

(54) THERMAL MASS FLOWMETER

(71) Applicant: KOREA RESEARCH INSTITUTE OF STANDARD AND SCIENCE, Daejeon (KR)

(72) Inventor: Seok Hwan Lee, Daejeon (KR)

(73) Assignee: KOREA RESEARCH INSTITUTE OF STANDARD AND SCIENCE, Daejeon (KR)

( * ) Notice: Subject to any disclaimer, the term of this patent is extended or adjusted under 35 U.S.C. 154(b) by 356 days.

(21) Appl. No.: 17/598,059

(22) PCT Filed: Feb. 24, 2021

(86) PCT No.: PCT/KR2021/002292
§ 371 (c)(1),
(2) Date: Sep. 24, 2021

(87) PCT Pub. No.: WO2022/055054
PCT Pub. Date: Mar. 17, 2022

(65) Prior Publication Data
US 2022/0236091 A1 Jul. 28, 2022

(30) Foreign Application Priority Data
Sep. 14, 2020 (KR) .................. 10-2020-0117796

(51) Int. Cl.
*G01F 1/684* (2006.01)
*A61M 5/168* (2006.01)

(52) U.S. Cl.
CPC .......... *G01F 1/6847* (2013.01); *A61M 5/168* (2013.01)

(58) Field of Classification Search
CPC .. G01F 1/68–699; G01F 1/661; G01F 1/7084; G01F 1/7086; A61M 5/168
See application file for complete search history.

(56) References Cited

U.S. PATENT DOCUMENTS

| 7,908,931 | B1 * | 3/2011 | Dam | G01F 1/7084 73/861.05 |
| 8,451,436 | B2 * | 5/2013 | Verjus | G01F 1/6847 356/213 |
| 8,784,367 | B2 * | 7/2014 | Dekker | G01F 15/005 604/890.1 |

(Continued)

FOREIGN PATENT DOCUMENTS

| GB | 601298 A | * 5/1948 |
| KR | 1020070115480 A | 12/2007 |

(Continued)

*Primary Examiner* — Justin N Olamit
(74) *Attorney, Agent, or Firm* — PnK IP LLC

(57) ABSTRACT

Proposed is a thermal mass flowmeter including: a heating unit configured to heat at least a portion of a medium in a tube from the outside of the tube; a first thermometer disposed at a first position that is a downstream side from the heating unit in a flow direction of the medium; a second thermometer disposed at a second position that is a downstream side further than the first thermometer from the heating unit; and a controller configured to calculate the flow rate of the medium flowing through the tube using a phase difference due to flow of the medium between first measurement data measured by the first thermometer and second measurement data measured by the second thermometer.

9 Claims, 4 Drawing Sheets

(56) References Cited

U.S. PATENT DOCUMENTS

| | | | | |
|---|---|---|---|---|
| 2009/0025473 A1* | 1/2009 | Imai | ...................... | G01F 1/7084 |
| | | | | 73/204.14 |
| 2011/0035959 A1 | 2/2011 | Gera, Jr. | | |
| 2022/0008637 A1* | 1/2022 | Kumar | ................... | A61B 5/026 |
| 2023/0243680 A1* | 8/2023 | Matsunaga | ............. | G01F 1/662 |
| | | | | 356/28 |

FOREIGN PATENT DOCUMENTS

| KR | 10-2008-0113362 A | 12/2008 |
|---|---|---|
| KR | 101321314 B1 | 10/2013 |
| KR | 1020180088136 A | 8/2018 |
| KR | 1020200102831 A | 9/2020 |

\* cited by examiner

THERMAL MASS FLOWMETER

TECHNICAL FIELD

The present disclosure relates to a thermal mass flowmeter and, more particularly, to a thermal mass flowmeter that makes it possible to measure the flow rate of a medium flowing through a tube in a dry type without cutting the tube.

BACKGROUND ART

In general, an infusion pump and a syringe pump are used as medicine injection pumps to inject a small amount of medicine into patients in the hospital. Such pumps are regulated to be used by each medical center itself, but they are regulated in an environment different from the sites where medicine is practically injected into patients.

For example, when medicine is injected into a patient, several medicines are simultaneously injected at a time by dividing a medicine delivery tube into branches to simultaneously deliver several medicines. Further, the internal pressure of a human body depends on the conditions of patients and the temperature and pressure conditions of operating rooms or wards are different, but these various conditions are not considered when medicine injection pumps are regulated due to practical limitations.

Accordingly, there is a need for a flowmeter that can monitor the actual injection amount of medicine. If is it possible to monitor the injection amount of medicine in real time, it is possible to perform feedback control by transmitting the injection amount to a medicine injection pump, so it is possible to improve accuracy of the medicine injection pump.

As the flowmeter that can monitor the injection amount of medicine, there are a wet type in which a tube should be cut and a flowmeter should be injected and a dry type in which it is possible to measure an injection amount outside a tube without cutting the tube.

SUMMARY OF INVENTION

Technical Problem

However, as for the wet type flowmeter of the related art, use is limited since a tube should be cut for installation, so it cannot be used in the hospital. Further, as for the dry type flowmeter of the related art, there is a dry type ultrasonic flowmeter that measures an injection amount without cutting a tube, but different regulation curves are required depending on the kinds of fluid, so there is a problem that when the kind of fluid is changed, the flow rate cannot be accurately measured.

The present disclosure has been made in an effort to solve the problems, and an objective of the present disclosure is to provide a thermal mass flowmeter that can be easily used by a doctor and a nurse because it can be easily detachably attached to a tube in a clamp-on type without cutting the tube and that can monitor in real time the flow rate of medicine practically injected in a patient because it can be practically used in various medical situations. However, the objective is only an example and the scope of the present disclosure is not limited thereto.

Solution to Problem

According to an embodiment of the present disclosure, a thermal mass flowmeter is provided. The thermal mass flowmeter may include: a heating unit configured to heat at least a portion of a medium in a tube from the outside of the tube; a first thermometer disposed at a first position that is a downstream side from the heating unit in a flow direction of the medium such that temperature distribution according to a flow speed of the medium heated by the heating unit in the tube can be measured; a second thermometer disposed at a second position that is a downstream side further than the first thermometer from the heating unit such that temperature distribution according to the flow speed of the medium heated by the heating unit in the tube can be measured; and a controller configured to calculate the flow rate of the medium flowing through the tube using a phase difference due to flow of the medium between first measurement data measured by the first thermometer and second measurement data measured by the second thermometer.

According to an embodiment of the present disclosure, the controller may include a heating unit variator configured to vary power of the heating unit such that a heating degree of the medium changes over time.

According to an embodiment of the present disclosure, the heating unit may include a laser emitter configured to emit a laser to be able to partially heat the medium in the tube.

According to an embodiment of the present disclosure, the first thermometer may include: a first infrared emitter installed at the first position and configured to radiate first infrared light to the medium in the tube; and a first infrared receiver installed opposite to the first infrared emitter with the tube therebetween and configured to sense the first infrared light that has passed through the medium.

According to an embodiment of the present disclosure, the second thermometer may include: a second infrared emitter installed at the second position and configured to radiate second infrared light to the medium in the tube; and a second infrared receiver installed opposite to the second infrared emitter with the tube therebetween and configured to sense the second infrared light that has passed through the medium.

According to an embodiment of the present disclosure, the tube may be a tube at least partially made of a transparent polymer material to be able to transmit the first infrared light emitted from the first infrared emitter and the second infrared light emitted from the second infrared emitter.

According to an embodiment of the present disclosure, the heating unit may further include: a first heater formed in a half-ring shape to cover a side of the tube and configured to partially heat the tube using thermal resistance; and a second heater formed in a half-ring shape to cover the other side of the tube opposite to the first heater and configured to partially heat the tube using thermal resistance.

According to an embodiment of the present disclosure, the thermal mass flowmeter may further include: a first body having a first retaining groove fixing at least a portion of the tube; and a second body having a second retaining groove receiving and fixing other portion of the tube, and combined with the first body to cover the tube.

According to an embodiment of the present disclosure, the first infrared emitter and the second infrared emitter may be installed at a side of the second retaining groove, and the first infrared receiver and the second infrared receiver may be installed at the other side of the second retaining groove to be opposite to the first infrared emitter and the second infrared emitter.

According to an embodiment of the present disclosure, the first heater may be installed at a side of the second retaining groove and the second heater may be installed at the other side of the second retaining groove to be opposite to the first heater.

According to an embodiment of the present disclosure, a magnetic body may be disposed on at least a portion of any one of the first body and the second body, a coupling portion may be formed on at least a portion of the other one of the first body and the second body, and the first body and the second body may be combined by coupling the magnetic body to the coupling portion.

Advantageous Effects of Invention

According to an embodiment of the present disclosure described above, the thermal mass flowmeter can be easily used by a doctor and a nurse because it can be easily detachably attached to a tube in a clamp-on type without cutting a thermal tube and can monitor in real time the flow rate of medicine practically injected in a patient because it can be practically used in various medical situations.

Further, feedback control is applied to a medicine injection pump on the basis of the monitored flow rate value of medicine, whereby the performance of the medicine injection pump can be improved. Accordingly, it is possible to achieve a thermal mass flowmeter that can inject an accurate amount of medicine into a patient and can secure stability for a patient. Obviously, the scope of the present disclosure is not limited to the effects.

DESCRIPTION OF EMBODIMENTS

Figure 1:
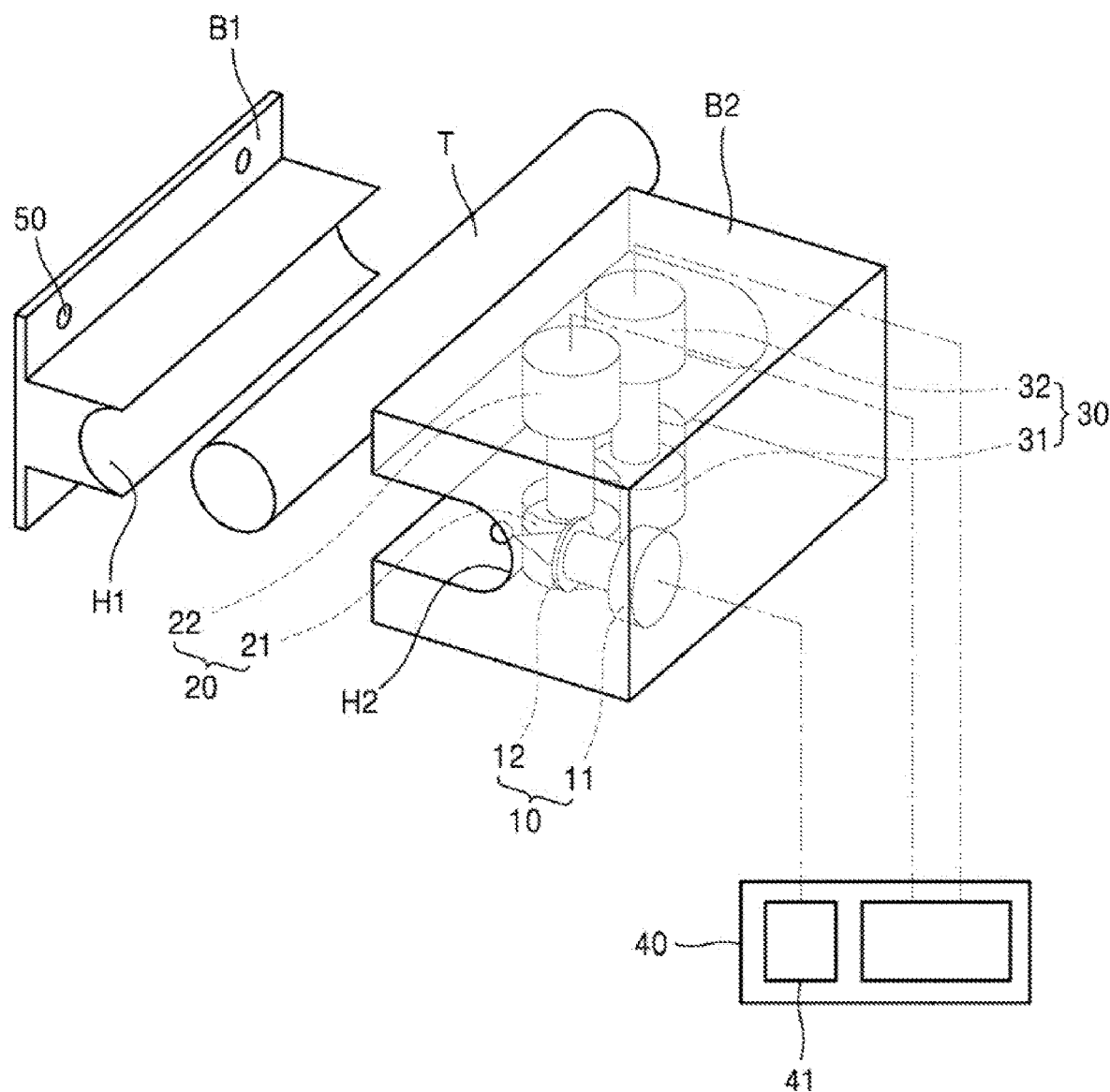
FIG. 1 is a perspective view showing a thermal mass flowmeter according to an embodiment of the present disclosure.

Hereinafter, several exemplary embodiments of the present disclosure are described in detail with reference to the accompanying drawings.

Embodiments of the present disclosure are provided to more completely explain the present disclosure to those skilled in the art, the following embodiments may be modified in various ways, and the scope of the present disclosure is not limited to the following embodiments. On the contrary, the embodiments are provided to make the present disclosure more substantial and complete and to fully transmit the spirit of the present disclosure to those skilled in the art. The thickness or size of each layer is exaggerated in the drawings for convenience and clarity of description.

Hereafter, embodiments of the present disclosure are described with reference to drawings schematically showing ideal embodiments. In the drawings, modifications of the shapes may be expected, for example, depending on the manufacturing technique and/or tolerance. Accordingly, embodiments describing the spirit of the present disclosure should not be construed as being limited to specific shapes of regions shown in the drawings, and should include, for example, changes in shape due to manufacturing.

Figure 2:
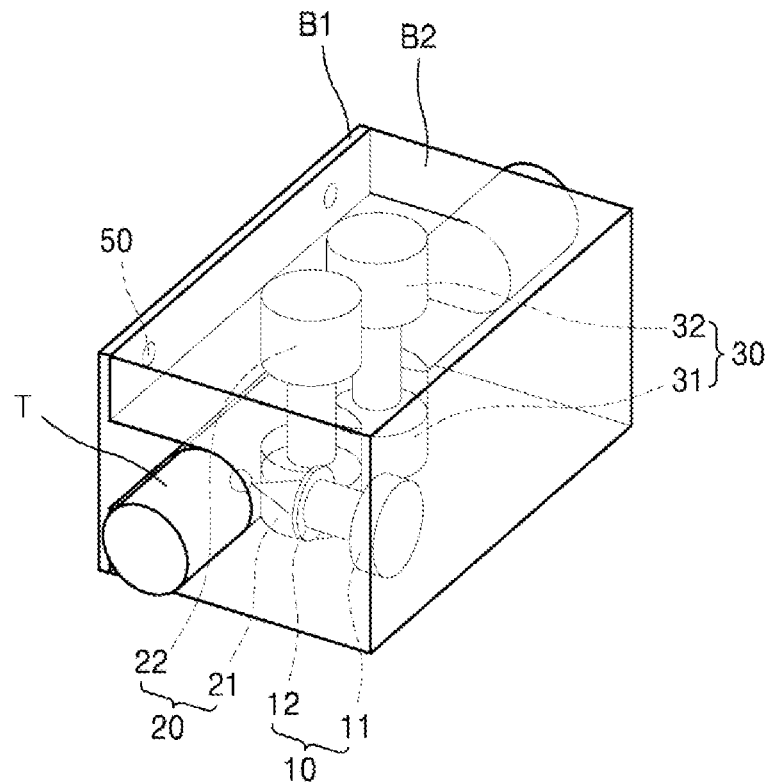
FIG. 2 is a perspective view showing that the thermal mass flowmeter of FIG. 1 has been clamped to a tube.

FIG. 1 is a perspective view showing a thermal mass flowmeter according to an embodiment of the present disclosure, and FIG. 2 is a perspective view showing that the thermal mass flowmeter of FIG. 1 has been clamped to a tube T.

First, as shown in FIG. 1, a thermal mass flowmeter according to an embodiment of the present disclosure, in a broad meaning, may include a first body B1, a second body B2, a heating unit 10, a first thermometer 20, and a second thermometer 30.

As shown in FIG. 1, the thermal mass flowmeter may include a first body B1 that has a first retaining groove H1 fixing at least a portion of a tube T and a second body B2 that has a second retaining groove H2 receiving and fixing other portion of the tube T and that is combined with the first body B1 to cover the tube T.

In detail, the first body B1 and the second body B2 may be structures having appropriate strength and durability to be able to receive and support the heating unit 10, the first thermometer 20, and the second thermometer 30. For example, the first body B1 and the second body B2 may be structures made of one or more selected from steel, stainless steel, aluminum, magnesium, zinc, and synthetic resin. However, the first body B1 and the second body B2 are not limited to FIG. 1 and may be members made of various materials that can receive and support the heating unit 10, the first thermometer 20, and the second thermometer 30.

A magnetic body 50 is disposed on at least a portion of any one of the first body B1 and the second body B2 and a coupling portion is formed on at least a portion of the other one of the first body B1 and the second body B2. Accordingly, the first body B1 and the second body B2 can be combined by coupling the magnetic body to the coupling portion.

For example, as shown in FIG. 2, a magnet may be disposed at a portion of the first body B1 as the magnetic body 50 and the coupling portion corresponding to the magnet may be made of a material that is attracted to a magnet, so the first body B1 and the second body B2 can be combined to cover the tube T.

Though not shown, a hinge portion may be formed at the joint between the first body B1 and the second body B2, so the second body B2 can be folded with respect to the first body B1. Other than the hinge portion, a folding portion that is made of thin synthetic resin, etc. and can be easily folded may be formed between the first body B1 and the second body B2 so that the second body B2 can be folded with respect to the first body B1.

Accordingly, the first body B1 and the second body B2 of the thermal mass flowmeter according to an embodiment of the present disclosure, as shown in FIG. 2, can receive the heating unit 10, the first thermometer 20 and the second thermometer 30, can be combined and easily detachably attached to the tube T in a clamp-on type, and can enable a doctor and a nurse to easily use the thermal mass flowmeter in the hospital.

The heating unit 10, which is a device for heating at least a portion of the medium in the tube T from the outside of the tube T, may be disposed in any one of the first body B1 and the second body B2.

The heating unit 10 can heat at least a portion of the medium in the tube T from the outside of the tube T. In detail, the heating unit 10 may include a laser emitter 11 that emits a laser L to be able to partially heat the medium in the tube T, a lens unit 12 that adjusts the focus such that the laser L generated by the laser emitter 11 can be radiated to the center of the tube T through which the medium flows, and a beam block 13 that is disposed opposite to the laser emitter 11 with the tube T therebetween to prevent the laser L emitted from the laser emitter 11 from leaking outside through the tube T.

The laser emitter 11 may be disposed in the second retaining groove H2 of the second body B2 and the beam block 13 may be disposed in the first retaining groove H1 of the first body B1 to be opposite to the laser emitter 11 such that the laser emitter 11 and the beam block 13 face each other when the first body B1 and the second body B2 are combined and clamped to the tube T.

Further, the laser emitter 11 may be disposed at a side of the second retaining groove H2 of the second body B2 and the beam block 13 may disposed at the other side of the second retaining groove H2 of the second body B2 to be opposite to the laser emitter 11 such that the laser emitter 11 and the beam block 13 face each other when the second body B2 is clamped with the first body B1 with the tube T inserted in the second retaining groove H2 of the second body B2.

Accordingly, when the laser L generated by the laser emitter 11 is radiated to the tube T with the focus adjusted on the inside of the tube T, it is possible to quickly increase the temperature of a portion of the medium in the tube T by partially heating the medium. Further, the beam block 13 disposed opposite to the laser emitter 11 with the tube T therebetween blocks the laser L that has passed through the tube T and the medium, thereby being able to prevent the laser L from leaking out of the tube T.

Though not shown, the heating unit 10 may include a first heater formed in a half-ring shape in the first retaining groove H1 of the first body B1 to cover a side of the tube T and partially heating the tube T using thermal resistance, and a second heater formed in a half-ring shape in the second retaining groove H2 of the second body B2 to cover the other side of the tube T opposite to the first heater and partially heating the tube T using thermal resistance.

Accordingly, when an accurate flow rate measurement value of the medium flowing through the tube T is not required, it is possible to achieve a thermal mass flowmeter at a lower cost using heaters that can partially heat the tube T using thermal resistance.

As shown in FIG. 2, the first thermometer 20 may be disposed at a first position that is a downstream side from the heating unit 10 in the flow direction of the medium such that temperature distribution according to the flow speed of the medium heated by the heating unit 10 in the tube T can be measured from the outside of the tube T. The second thermometer 20 may be disposed at a second position that is a downstream side further than the first thermometer 20 from the heating unit 10 such that temperature distribution according to the flow speed of the medium heated by the heating unit 10 in the tube T can be measured from the outside of the tube T.

More specifically, the first thermometer 20 may include: a first infrared emitter 21 that is installed at the first position, which is a downstream side from the heating unit 10 in the flow direction of the medium, and radiates first infrared light IR1 to the medium in the tube T; and a first infrared receiver 22 that is installed opposite to the first infrared emitter 21 with the tube T therebetween and senses first infrared light IR1 that has passed through the medium.

The second thermometer 30 may include: a second infrared emitter 31 that is installed at the second position, which is a downstream side from the heating unit 10 in the flow direction of the medium, and radiates second infrared light IR2 to the medium in the tube T; and a second infrared receiver 32 that is installed opposite to the second infrared emitter 31 with the tube T therebetween and senses second infrared light IR2 that has passed through the medium.

The distance from the heating unit 10 to the second position where the second thermometer 30 is disposed may be two times the distance from the heating unit 10 to the first position. Accordingly, the flow rate of the medium can be calculated from the distance values and data measured by the first thermometer 20 and the second thermometer 30.

The first infrared emitter 21 and the second infrared emitter 31 may be installed at a side of the second retaining groove H2 of the second body B2, and the first infrared receiver 22 and the second infrared receiver 32 may be installed at the other side of the second retaining groove H2 of the second body H2 to be opposite to the first infrared emitter 21 and the second infrared emitter 31 such that the first and second infrared emitters 21 and 32 and the first and second infrared receives 22 and 32 face each other.

The tube T may be a tube made of a transparent polymer material to be able to easily transmit the laser L emitted from the laser emitter 21, the first infrared light IR1 of the first infrared emitter 21, and the second infrared light IR2 of the second infrared emitter 31.

Accordingly, when the infrared light IR1 and the second infrared light IR2 emitted from the first infrared emitter 21 and the second infrared emitter 31 pass through the medium heated in the tube T by a laser L, the degrees of the beams of infrared light IR1 and IR2 that are absorbed in the medium depend on the temperature of the medium, so temperature can be measured using the difference.

A controller 40 connected to the first thermometer 20 and the second thermometer 30 can measure the flow rate of the medium flowing through the tube T by receiving sensing signals from the first infrared receiver 22 and the second infrared receiver 32 and measuring the temperature distribution around the heating unit 10.

Figure 3:
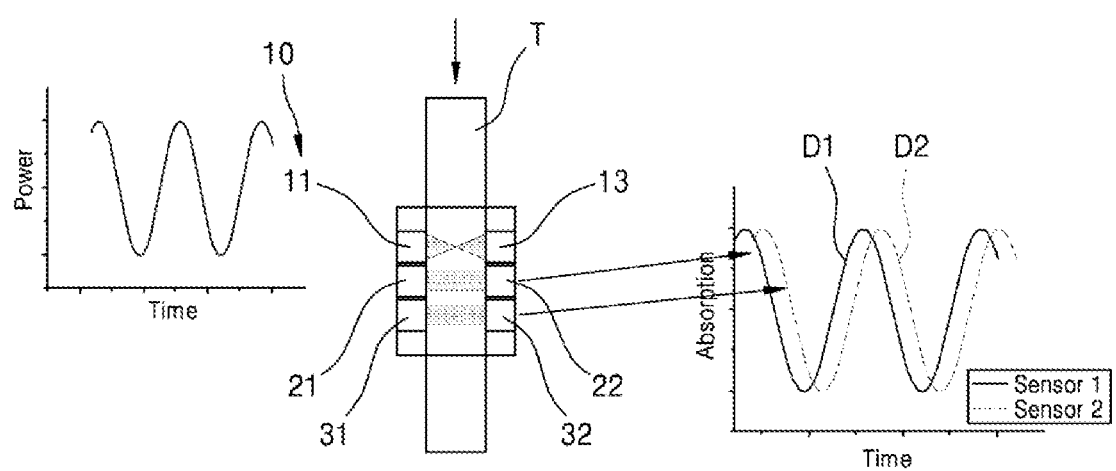
FIGS. 3 and 4 are cross-sectional views schematically showing data measured by the thermal mass flowmeter according to several embodiments of the present disclosure.

For example, using this principle, as shown in FIG. 3, it is possible to quickly increase the temperature of the medium at any one point in the tube T using the laser L emitted from the laser emitter 11, and in this case, temperature distribution due to a large temperature difference can be measured through the first thermometer 20 and the second thermometer 30. Since the temperature distribution depends on the flow speed of the medium flowing through the tube T, the controller 40 can calculate the flow rate of the medium flowing through the tube T using the temperature distribution.

Accordingly, the thermal mass flowmeter according to an embodiment of the present disclosure can be easily used by a doctor and a nurse in the hospital because it can be easily detachably attached to a tube T in a clamp-on type in a dry type without cutting the tube T, and can monitor in real time the flow rate of medicine practically injected into a patient through the controller because it can be practically used in various medical situations.

Further, feedback control is applied to a medicine injection pump on the basis of the monitored flow rate value of medicine, whereby the performance of the medicine injection pump can be improved. Accordingly, it is possible to achieve a thermal mass flowmeter that can inject an accurate amount of medicine into a patient and can secure stability for a patient.

Figure 4:
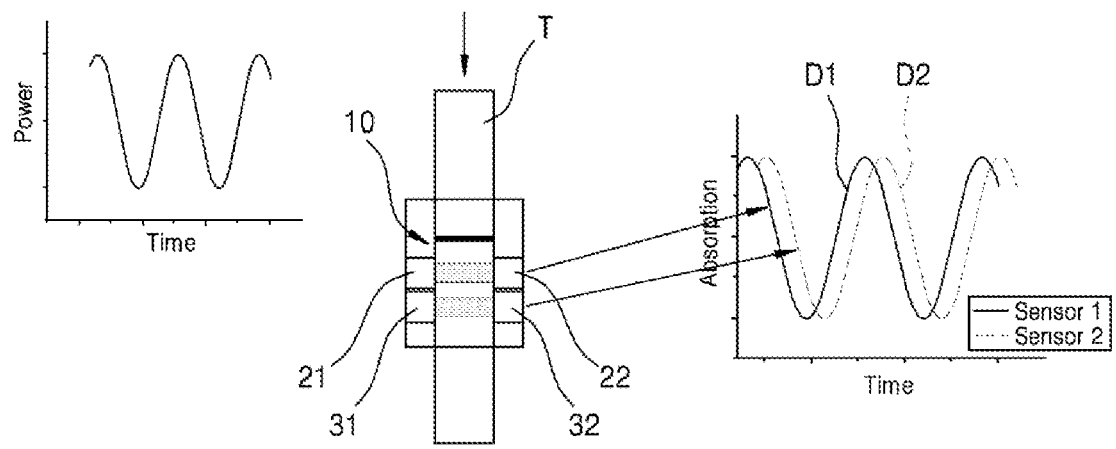

FIGS. 3 and 4 are cross-sectional views schematically showing data measured by the thermal mass flowmeter according to several embodiments of the present disclosure.

The controller 40 can calculate the flow rate of the medium flowing through the tube T using a phase difference due to flow of the medium between first measurement data D1 measured by the first thermometer 20 and second measurement data D2 measured by the second thermometer 30.

The controller 40 is connected to the heating unit 10, the first thermometer 20, and the second thermometer 30, thereby being able to separately control the devices or transmit/receive measured data.

The controller 40 may include a heating unit variator 41 that varies the power of the heating unit 10 such that the heating degree of the medium changes over time. Though not shown, the controller 40 may further include a receiver that receives measured data and a calculator that calculates the flow rate of the medium on the basis of the data received by the receiver.

The heating unit variator 41 can change the heating degree over time by varying the power of the heating unit 10 like a sine wave. Accordingly, as the medium flows, the data measured by the first thermometer 20 and the second thermometer 30 at the downstream side radiated from the heating unit 10 may be received in similar waveforms in accordance with variation signals. Further, a phase difference may be generated in the data measured by the first thermometer 20 and the second thermometer 30 due to a change in flow of the medium.

For example, as shown in FIGS. 3 and 4, the controller 40 can vary the power of the heating unit 10 in a sine wave for heating through the heating unit variator 41, and the first data D1 and the second data D2 received in the first infrared receiver 22 and the second infrared receiver 32 at the downstream side from the point radiated with heating unit 10 may also be measured in sine waveforms.

There is a time difference when measuring the first data D1 and the second data D2 due to movement of the medium, and accordingly, the phase difference may be generated.

The calculator can obtain a relationship with the flow rate by applying Fourier Transform on the first data D1 and the second data D2 that have the phase difference, and it is possible to measure the flow rate of the medium in a non-contact manner using the relationship.

Hereafter, an experimental example employing the spirit described above is described to help understand the present disclosure. However, the following experimental example is provided only to help understand the present disclosure and the present disclosure is not limited to the following experimental example.

Figure 5:
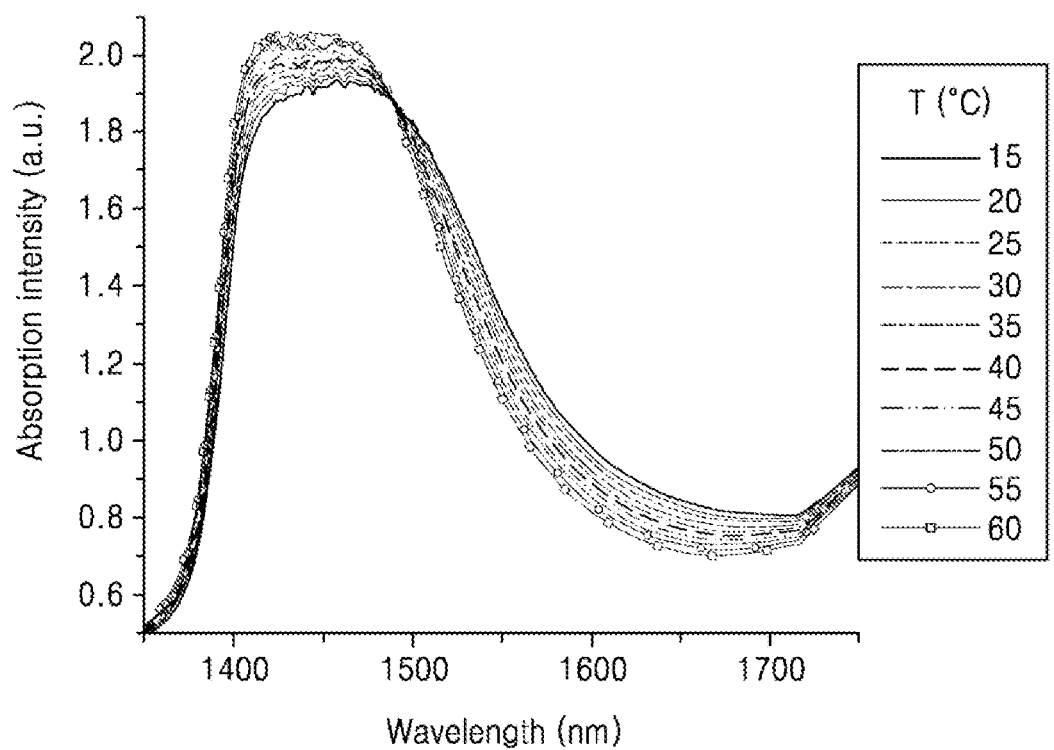
FIG. 5 is a graph showing a spectrum according to temperature.
Figure 6:
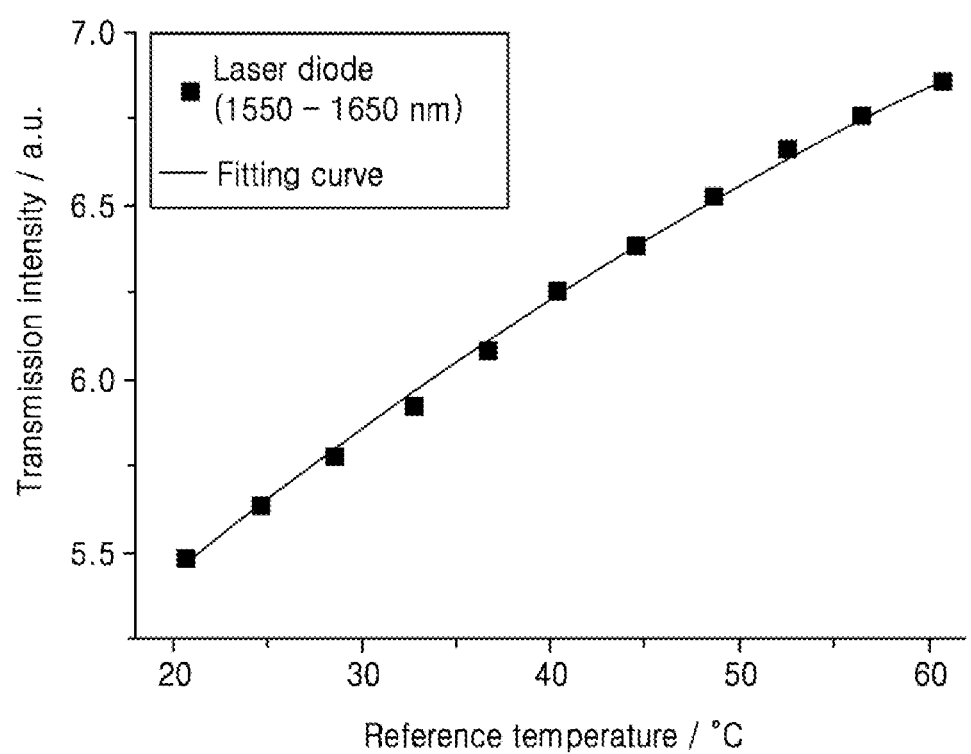
FIG. 6 is a graph showing the result measured using a diode laser.

FIG. 5 is a graph showing a spectrum according to temperature and FIG. 6 is a graph showing the result measured using a diode laser.

In the experimental example, a halogen lamp was used for a temperature measurement experiment using infrared light and a spectrum according to temperature was measured by a spectroscope. The spectroscope used in the experiment was AROpix spectroscope that can measure wavelengths from 900 nm to 2600 nm. Light from the halogen lamp was sent to an optical fiber through an IV set solution, which is used for medicine injection, and was then connected back to the spectroscope for measurement. The medium used herein was DI water and temperature in a medium storage chamber before measurement was measured.

As shown in FIG. 5, it can be seen that as the temperature increases, the spectrum measured in accordance with the temperature of the DI water shifts left downward between 1500 nm and 1700 nm, and it is possible to measure the temperature inside the tube in a non-contact manner using this characteristic.

FIG. 6 shows a temperature measurement result using a diode laser. Temperature was measured by means of a laser diode that emits light of a wavelength of 1550 nm to 1650 nm and a photodetector that measures the light, using the principle in which an infrared absorption spectrum shifts in accordance with temperature, as shown in FIG. 5. According to the measurement result, the absorptivity has linearity according to temperature, so it is possible to measure the temperature of the fluid in the tube in a non-contact manner using this characteristic.

Therefore, the thermal mass flowmeter according to an embodiment of the present disclosure can vary and increase the temperature of the medium at any one point in the tube T using the laser L emitted from the laser emitter 11, and temperature distribution due to a temperature difference over time can be measured through the first thermometer 20 and the second thermometer 30.

The graph of the temperature distribution measured by the first thermometer 20 and the second thermometer 30 has a phase difference, so it is possible to calculate the flow rate of the medium flowing through the tube T using the phase difference.

Accordingly, the thermal mass flowmeter according to an embodiment of the present disclosure can be easily used by a doctor and a nurse in the hospital because it can be easily detachably attached to a tube T in a clamp-on type without cutting the tube T, and can monitor in real time the flow rate of medicine practically injected into a patient through the controller because it can be practically used in various medical situations.

Further, feedback control is applied to a medicine injection pump on the basis of the monitored flow rate value of medicine, whereby the performance of the medicine injection pump can be improved. Accordingly, it is possible to achieve a thermal mass flowmeter that can inject an accurate amount of medicine into a patient and can secure stability for a patient.

Although the present disclosure has been described with reference to the exemplary embodiments illustrated in the drawings, those are only examples and may be changed and modified into other equivalent exemplary embodiments from the present disclosure by those skilled in the art. Therefore, the technical protective region of the present invention should be determined by the scope described in claims.

INDUSTRIAL APPLICABILITY

A thermal mass flowmeter according to an embodiment of the present disclosure described above can be easily used by a doctor and a nurse because it can be easily detachably attached to a tube in a clamp-on type without cutting a thermal tube and can monitor in real time the flow rate of medicine practically injected in a patient because it can be practically used in various medical situations. Accordingly, it is possible to inject an accurate amount of medicine into a patient and secure stability for a patient.

The invention claimed is:

1. A thermal mass flowmeter comprising:
   a heating unit configured to heat at least a portion of a medium in a tube from an outside of the tube;
   a first thermometer disposed at a first position that is a downstream side from the heating unit in a flow direction of the medium, the first thermometer being configured to measure temperature distribution according to a flow speed of the medium heated by the heating unit in the tube;

a second thermometer disposed at a second position that is a downstream side further than the first thermometer from the heating unit, the second thermometer being configured to measure temperature distribution according to the flow speed of the medium heated by the heating unit in the tube;

a controller configured to calculate a flow rate of the medium flowing through the tube using a phase difference between first measurement data measured by the first thermometer and second measurement data measured by the second thermometer;

a first body having a first retaining groove configured to fix at least one portion of a circumferential area of the tube; and a second body having a second retaining groove configured to receive and fix another portion of the circumferential area of the tube opposite to the at least one portion of the circumferential area of the tube, the second body having a protruding portion protruding longer than a diameter of the tube, wherein the protruding portion of the second body has an internal space configured to be open to an outside and the second retaining groove is defined in the internal space, wherein the first body has a protruding portion configured to be inserted through the internal space of the second body toward the second retaining groove, the protruding portion of the first body having the first retaining groove, wherein the first body is configured to be combined with the second body by insertion of the protruding portion of the first body through the internal space of the second body to cover the tube, wherein an inner surface of the first retaining groove is configured to closely contact the at least one portion of the circumferential area of the tube and an inner surface of the second retaining groove is configured to closely contact the another portion of the circumferential area of the tube opposite to the at least one portion of the circumferential area of the tube, the first retaining groove and the second retaining groove thereby being configured to fix the at least one portion and the another portion of the circumferential area of the tube, wherein the heating unit includes a laser emitter configured to emit a laser to be able to partially heat the medium in the tube, a lens configured to adjust a focus of the laser generated by the laser emitter to radiate the laser to a center of the tube through which the medium flows, and a beam block disposed opposite to the laser emitter with the tube therebetween to prevent the laser emitted from the laser emitter from leaking outside through the tube, wherein the first thermometer includes:
 a first infrared emitter configured to radiate first infrared light to the medium in the tube; and
 a first infrared receiver disposed opposite to the first infrared emitter with the tube therebetween and configured to sense the first infrared light that has passed through the medium, wherein the second thermometer includes:
 a second infrared emitter configured to radiate second infrared light to the medium in the tube; and
 a second infrared receiver disposed opposite to the second infrared emitter with the tube therebetween and configured to sense the second infrared light that has passed through the medium, and wherein the first infrared emitter and the second infrared emitter are disposed at a side of the second retaining groove, and the first infrared receiver and the second infrared receiver are disposed at another side of the second retaining groove to be opposite to the first infrared emitter and the second infrared emitter.

2. The thermal mass flowmeter of claim 1, wherein the controller includes a heating unit variator configured to vary power of the heating unit such that a heating degree of the medium changes over time.

3. The thermal mass flowmeter of claim 1, wherein the first infrared emitter is disposed at the first position.

4. The thermal mass flowmeter of claim 3, wherein the second infrared emitter is disposed at the second position.

5. The thermal mass flowmeter of claim 4, wherein at least a portion of the tube has a transparent polymer material to be able to transmit the first infrared light emitted from the first infrared emitter and the second infrared light emitted from the second infrared emitter.

6. The thermal mass flowmeter of claim 4, wherein a magnetic body is disposed on at least a portion of any one of the first body and the second body,
 a coupling portion is disposed on at least a portion of the other one of the first body and the second body, and
 the first body and the second body are configured to be combined by coupling the magnetic body to the coupling portion.

7. A thermal mass flowmeter comprising:
 a heating unit configured to heat at least a portion of a medium in a tube from an outside of the tube;
 a first thermometer disposed at a first position that is a downstream side from the heating unit in a flow direction of the medium, the first thermometer being configured to measure temperature distribution according to a flow speed of the medium heated by the heating unit in the tube;
 a second thermometer disposed at a second position that is a downstream side further than the first thermometer from the heating unit, the second thermometer being configured to measure temperature distribution according to the flow speed of the medium heated by the heating unit in the tube;
 a controller configured to calculate a flow rate of the medium flowing through the tube using a phase difference between first measurement data measured by the first thermometer and second measurement data measured by the second thermometer;
 a first body having a first retaining groove configured to fix at least one portion of a circumferential area of the tube; and
 a second body having a second retaining groove configured to receive and fix another portion of the circumferential area of the tube opposite to the at least one portion of the circumferential area of the tube, the second body having a protruding portion protruding longer than a diameter of the tube,
 wherein the protruding portion of the second body has an internal space configured to be open to an outside and the second retaining groove is defined in the internal space,
 wherein the first body has a protruding portion configured to be inserted through the internal space of the second body toward the second retaining groove, the protruding portion of the first body having the first retaining groove, wherein the first body is configured to be combined with the second body by insertion of the protruding portion of the first body through the internal space of the second body to cover the tube, and wherein an inner surface of the first retaining groove is configured to closely contact the at least one portion of the circumferential area of the tube and an inner surface of the second retaining groove is configured to closely contact the another portion of the circumferential area of the tube opposite to the at least one portion of the circumferential area of the tube, the first retaining groove and the second retaining groove thereby being configured to fix the at least one portion and the another portion of the circumferential area of the tube, wherein the heating unit further includes:
  a first heater having a half-ring shape to cover a side of the tube and configured to partially heat the tube using thermal resistance; and
  a second heater having a half-ring shape to cover another side of the tube opposite to the first heater and configured to partially heat the tube using thermal resistance, wherein the first thermometer includes:
  a first infrared emitter configured to radiate first infrared light to the medium in the tube; and
  a first infrared receiver disposed opposite to the first infrared emitter with the tube therebetween and configured to sense the first infrared light that has passed through the medium, wherein the second thermometer includes:
  a second infrared emitter configured to radiate second infrared light to the medium in the tube; and
  a second infrared receiver disposed opposite to the second infrared emitter with the tube therebetween and configured to sense the second infrared light that has passed through the medium, and wherein the first infrared emitter and the second infrared emitter are disposed at a side of the second retaining groove, and the first infrared receiver and the second infrared receiver are disposed at another side of the second retaining groove to be opposite to the first infrared emitter and the second infrared emitter.

8. The thermal mass flowmeter of claim 7, wherein the first heater is disposed at a side of the second retaining groove and the second heater is disposed at another side of the second retaining groove to be opposite to the first heater.

9. The thermal mass flowmeter of claim 7, wherein a magnetic body is disposed on at least a portion of any one of the first body and the second body,
  a coupling portion is disposed on at least a portion of the other one of the first body and the second body, and
  the first body and the second body are configured to be combined by coupling the magnetic body to the coupling portion.

* * * * *